(12) United States Patent  
Iwasaki et al.

(10) Patent No.: US 8,491,308 B2  
(45) Date of Patent: Jul. 23, 2013

(54) ENDURANCE TEST APPARATUS FOR MEDICAL INSTRUMENT AND ENDURANCE TEST METHOD

(75) Inventors: Kiyotaka Iwasaki, Tokyo (JP); Mitsuo Umezu, Tokyo (JP); Akira Nishikohri, Tokyo (JP); Shunsuke Tsubouchi, Tokyo (JP)

(73) Assignee: Waseda University, Tokyo (JP)

( * ) Notice: Subject to any disclaimer, the term of this patent is extended or adjusted under 35 U.S.C. 154(b) by 701 days.

(21) Appl. No.: 12/676,735

(22) PCT Filed: Feb. 29, 2008

(86) PCT No.: PCT/JP2008/053636  
§ 371 (c)(1),  
(2), (4) Date: Jun. 22, 2010

(87) PCT Pub. No.: WO2009/031329  
PCT Pub. Date: Mar. 12, 2009

(65) Prior Publication Data  
US 2010/0291524 A1 Nov. 18, 2010

(30) Foreign Application Priority Data  
Sep. 7, 2007 (JP) .................................. 2007-233460

(51) Int. Cl.  
*G09B 23/28* (2006.01)

(52) U.S. Cl.  
USPC ............ 434/272; 434/267; 434/268; 434/262

(58) Field of Classification Search  
USPC ........................... 434/268, 272; 600/301, 485  
See application file for complete search history.

(56) References Cited

U.S. PATENT DOCUMENTS  
2006/0230814 A1 10/2006 Keeble

FOREIGN PATENT DOCUMENTS

| JP | 2000-342692 A | 12/2000 |
|----|---------------|---------|
| JP | 2005-278828 A | 10/2005 |
| JP | 2006-509569 T | 3/2006 |
| JP | 2006-192227 A | 7/2006 |
| JP | 2006-192228 A | 7/2006 |
| JP | 2006-192229 A | 7/2006 |
| JP | 2006-192230 A | 7/2006 |

OTHER PUBLICATIONS

A. Nishikohri et al, "Development of an Accelerated Fatigue Tester to Evaluate Durability Performance of Vascular Stent," Lecture Transcript of the Japan Society of Mechanical Engineers 19th Bioengineering Koenkai, Jan. 2007, No. 06-65, pp. 80-81.  
K. Iwasaki et al, "Durability Assessment of Peripheral Self-Expandable Stents Using Waseda Accelerated Fatigue Tester Under an In-vivo Equivalent Multi-loading Environment," Lecture Transcripts of the Japan Society of Mechanical Engineers 2007 Nendo Nenji Taikai, No. 07-1, pp. 301-302.  
International Search Report of PCT/JP2008/053636, mailing date of Apr. 8, 2008.

*Primary Examiner* — Xuan Thai  
*Assistant Examiner* — Banafsheh Hadizonooz  
(74) *Attorney, Agent, or Firm* — Westerman, Hattori, Daniels & Adrian, LLP

(57) ABSTRACT

It is intended to provide an endurance test apparatus whereby the behaviors of a vessel caused by a biomechanical burden can be simulated using a relatively simple constitution so that the endurance of a medical instrument (for example, a stent or an artificial vessel after anastomosis) can be tested in a similar state to an actual vessel, and an endurance test method therefor. Namely, an endurance test apparatus (10) comprises a simulated vessel (31) made of an elastic body, first and second holding members (32, 33) respectively supporting the both ends in the axial direction of the simulated vessel (31) and making the both ends relatively rotatable and interval-adjustable, and first and second motors (14, 15) operating these holding members (32, 33). The simulated vessel (31) is supported by the first and second holding members (32, 33) in a state stretched from its inherent length under a tensile force. Due to the driving motors (14, 15), the holding members (32, 33) elongate and contract the simulated vessel (31), which is in the stretched state as described above, while twisting it.

3 Claims, 3 Drawing Sheets

ENDURANCE TEST APPARATUS FOR MEDICAL INSTRUMENT AND ENDURANCE TEST METHOD

TECHNICAL FIELD

The present invention relates to an endurance test apparatus for medical instruments and to an endurance test method. More particularly, the present invention relates to an endurance test apparatus and an endurance test method for evaluation of the endurance of a medical instrument such as a stent inserted in a blood vessel, or an artificial blood vessel anastomosed at the time of operative procedure training, while the behavior of the blood vessel resulting from biomechanical loads is being considered.

BACKGROUND ART

As a medical instrument used for a treatment in the event of narrowing of blood vessel, a tubular metallic member in meshwork form called a stent is known. This stent is held in a narrowing portion of a blood vessel for a long period of time to continuously extend the narrowing portion. In doing an endurance test on the stent, therefore, it is important to consider the state in which the stent is held in a blood vessel. However, it is impossible to actually do such an endurance test in a human body and there is a need to do such a test with a mechanical apparatus simulating features of a human body.

As an apparatus for evaluating the performance of stents, a stent performance evaluation simulator disclosed in Patent Document 1 and a stent mechanical characteristic measuring apparatus disclosed in Patent Document 2 are known.

The stent performance evaluation simulator according to Patent Document 1 has a circuit configuration simulating coronary circulation and is provided with a fluid path in closed loop form, a pump for producing a pulsating flow in a fluid circulating through the fluid path, a branch line branching at an intermediate position in the fluid path, and a flexible tube provided at an intermediate position in the branch line. A stent to be evaluated is held in the flexible tube and is subjected to the fluid in which the pulsating flow is produced. With this simulator, therefore, the endurance of the stent can be examined under conditions close to the blood pulsating conditions in actual use of the stent.

The stent mechanical characteristic measuring apparatus according to Patent Document 2 is an apparatus which directly pulls a stent from one end side of the same to derive a correlation between a load acting on the stent and the stretched length, whereby the performance of the stent is evaluated from a mechanical point of view.

In a case where a stent is held in a superficial femoral artery (SFA) in a femur of a human body, the vessel moves more largely than other portions and a large load can act easily on the stent held in the vessel, because the superficial femoral artery is a vessel having dynamic factors. In a case where a stent is held in a superficial femoral artery, therefore, it can damage more easily with time than in other portions. More specifically, biomechanical loads, such as torsion, contraction or extension, act on the superficial femoral artery, for example, as a result of an external force due to a motion or the like of a leg portion and a change in blood pressure, and the stent use environment is worse than in other vessel portions. From the stent held in the superficial femoral artery differing as a user environment from other portions, therefore, a result of an endurance test different from the result of actual use is produced to reduce the reliability of the endurance test, unless the endurance test is conducted by considering the above-described biomechanical loads.

Each of the simulator according to the above-mentioned Patent Document 1 and the apparatus according to the above-mentioned Patent Document 2, however, is incapable of simulating the behavior of a blood vessel resulting from the above-described biomechanical loads specific to the superficial femoral artery and correctly evaluating the endurance of a stent held in the superficial femoral artery.

With respect to a coronary artery stent held in the coronary artery, an instance of damage in a state of being held in a patient has also been reported. There is a demand for a system capable of predicting the endurance in an environment in which the above-described biomechanical loads are simulated.

Further, when a doctor or a medical student goes into anastomosis procedure training by inosculating an artificial blood vessel for training already put on the market, no apparatus exists with which the endurance of an inosculated portion of the obtained inosculated artificial blood vessel is tested by causing the artificial blood vessel to behave in the same way as in the actual postoperative state of a patient, and it is impossible to make an objective evaluation of the anastomosis procedure by considering the behavior of the blood vessel.

Patent document 1: Japanese Patent Publication No. 2000-342692
Patent document 2: Japanese Patent Publication No. 2005-278828

DISCLOSURE OF THE INVENTION

Problem to be Solved by the Invention

The applicant of the present invention has already proposed blood vessel motion simulators constructed so as to enable reproduction of the above-described biomechanical loads (Japanese Patent Application Nos. 2006-192227, 2006-192228, 2006-192229, and 2006-192230).

The inventors of the present invention have further pursued studies to find that each of blood vessels in a leg including the superficial femoral artery is in a tensioned state in which a predetermined tensile stress acts, and that an action such as a walk causes torsion, extension and contraction to act complexly as the above-described biomechanical loads while the blood vessel is in the tensioned state.

The present invention has been achieved by modifying the already-proposed inventions on the basis of such an inventors' finding, and an object of the present invention is to provide an endurance test apparatus for medical instruments and an endurance test method capable of simulating the behavior of a blood vessel resulting from biomechanical loads with a comparatively simple arrangement, and testing the endurance of a medical instrument such as a stent or an artificial blood vessel after anastomosis in a state similar to that in the actual blood vessel.

Means for Solving the Problems (1) To achieve the above-described object, the present invention adopts a construction having a simulated blood vessel formed of a predetermined elastic body, supporting means for supporting opposite end portions of the simulated blood vessel in the direction of extension of the simulated blood vessel, the supporting means operating so that the two end portions are relatively rotatable and able to move closer to and away from each other, and drive means for operating the supporting means, wherein the simulated blood vessel is supported by the supporting means in a state of being elongated from a natural-length state under the action of a tensile force, and wherein the supporting means is driven by the drive means to cause elongating/shortening deformation in the simulated blood vessel in the elongated state while simultaneously causing torsion deformation in the simulated blood vessel.

(2) It is preferable to adopt a construction in which the simulated blood vessel is supported by the supporting means in the elongated state disabling generation of bending deformation at the time of the elongating/shortening deformation.

(3) Also, the present invention adopts a method including repeatedly performing an operation to cause torsion deformation in a simulated blood vessel formed of a predetermined elastic body and to simultaneously cause elongating/shortening deformation in the simulated blood vessel while a predetermined tensile force is being applied to the simulated blood vessel.

Advantages of the Invention

According to the present invention, a twisting operation and an elongating/shortening operation are performed on the simulated blood vessel under the action of a tensile stress, thereby imparting to the simulated blood vessel a behavior corresponding to the behavior of the actual superficial femoral artery found by the inventors of the present invention. Therefore, an endurance test on a stent to be used in the superficial femoral artery can be conducted by holding the stent in the simulated blood vessel. Also, if an artificial blood vessel inosculated at the time of anastomosis procedure training is applied as a simulated blood vessel, a behavior corresponding to that of the superficial femoral artery or the like can be imparted to the artificial blood vessel. Therefore, the endurance of the artificial blood vessel after anastomosis can be tested under conditions close to the actual conditions, and the anastomosis procedure training can be evaluated from the results of the endurance test. Further, when the simulated blood vessel has elongating/shortening deformation after filling the interior of the simulated blood vessel with a liquid, the liquid pressure changes with the elongating/shortening deformation. In this way, the same pulsating state as that in the actual blood vessel can be created in the simulated blood vessel. There is, therefore, no need to adopt a circulation circuit construction simulating a living body to produce the pulsating state, and variation in blood pressure in the blood vessel can be simulated by means of a simple apparatus construction. In general, according to the present invention, the behavior of the superficial femoral artery or the like under biomechanical loads can be simulated by means of a simple construction, and an evaluation of the endurance of a stent, an objective evaluation of an anastomosis procedure or the like considering the behavior can be made in a short time period.

In particular, by adopting a construction such as shown in (2) in the above, the possibility of occurrence of a sag, i.e., bending deformation in the simulated blood vessel, with elongating/shortening deformation when the simulated blood vessel has elongating/shortening deformation is eliminated, so that a twisting action and elongating/shortening action, which are the behaviors of the superficial femoral artery or the like, can be produced with reliability.

In the claims and the specification of the present invention, "torsion" denotes twisting in a direction about the axis of a simulated blood vessel extending in the direction of extension, unless otherwise noted. Also, "elongating/shortening", extension", "contraction" and "tension" denote elongating/ shortening, extension, contraction and tension in the above-described axial direction unless otherwise noted.

DESCRIPTION OF SYMBOLS

10 Endurance test apparatus
14 First motor (drive means)
15 Second motor (drive means)
31 Simulated blood vessel
32 First holding member (supporting means)
33 Second holding member (supporting means)

BEST MODE FOR CARRYING OUT THE INVENTION

An embodiment of the present invention will be described with reference to the drawings.

Figure 1:
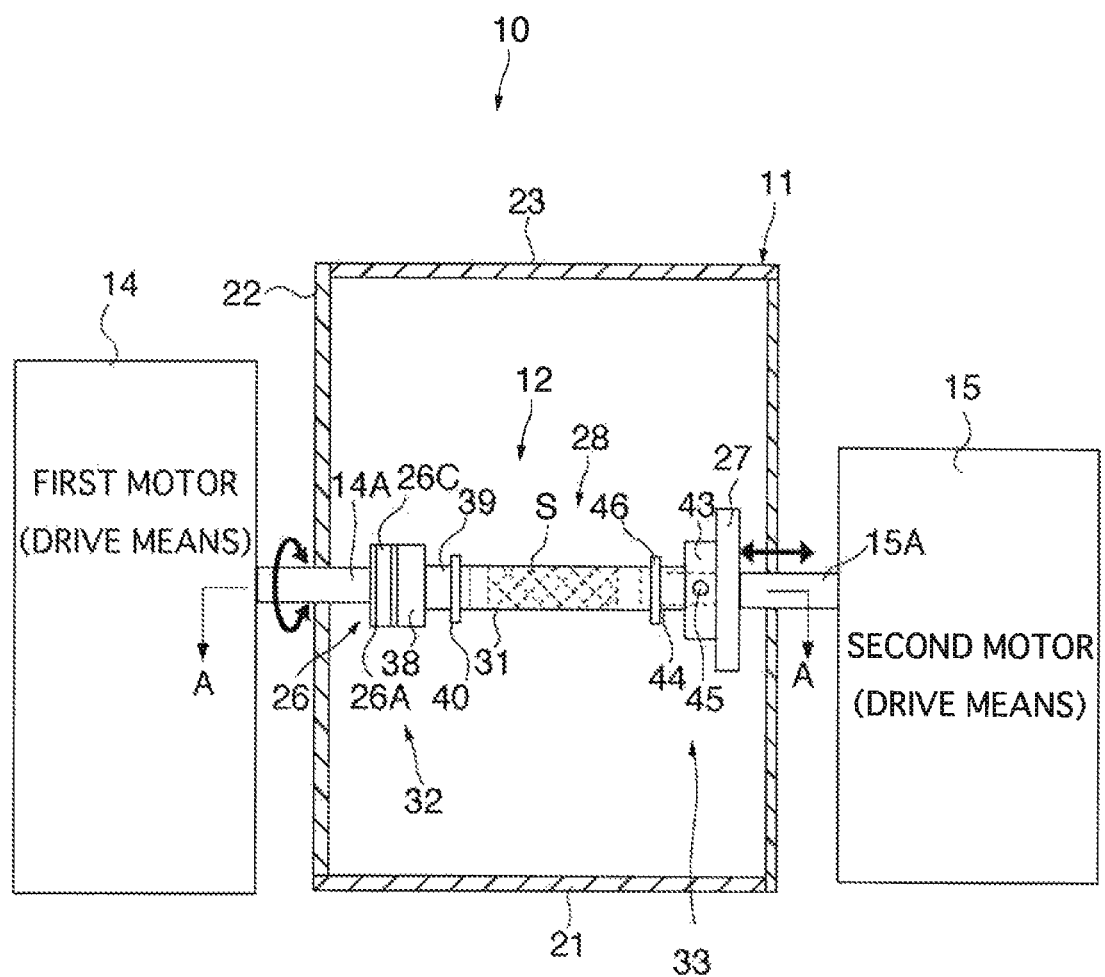
FIG. 1 is a schematic sectional front view of a blood vessel action simulator according to the present embodiment.
Figure 2:
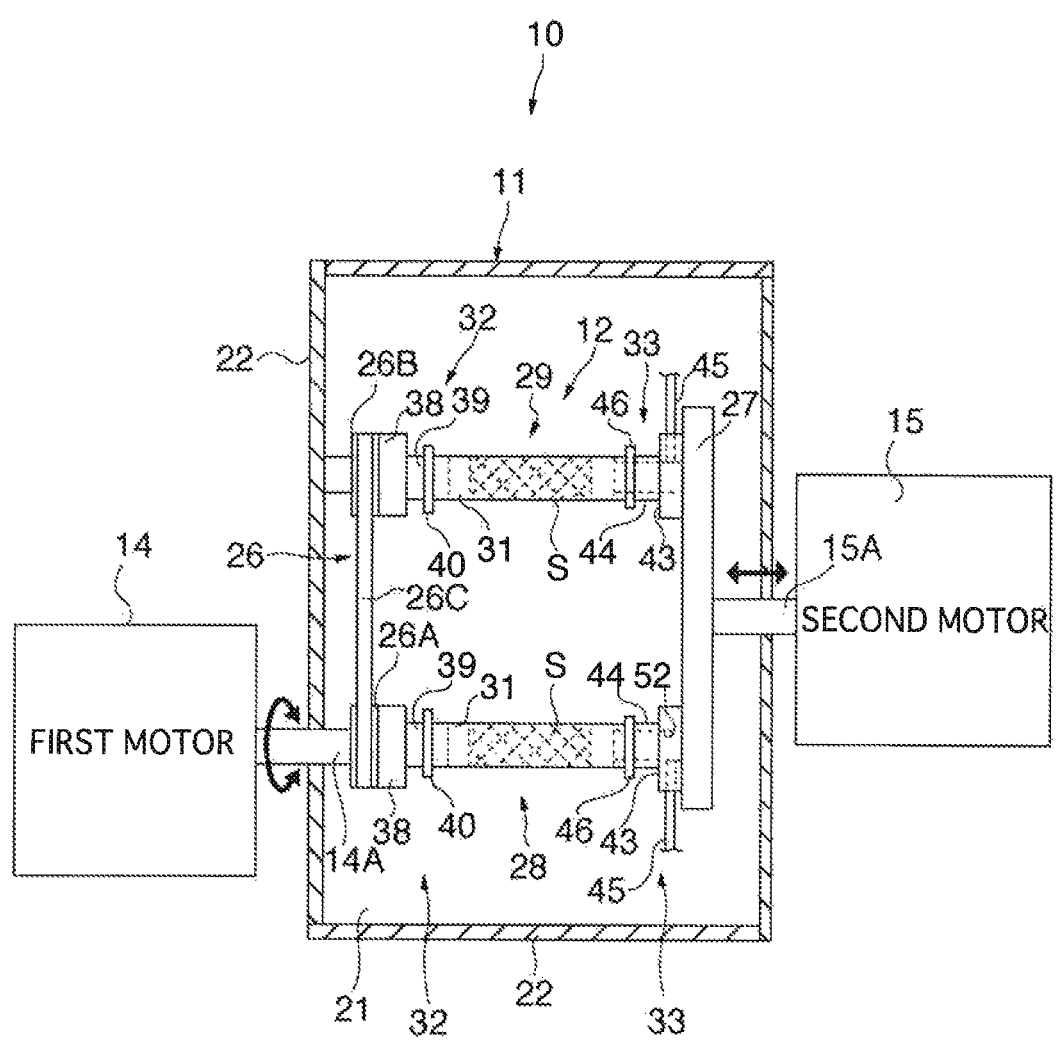
FIG. 2 is a schematic sectional plain view of the blood vessel action simulator.

FIG. 1 shows a schematic sectional front view of an endurance test apparatus according to the present embodiment. FIG. 2 shows a schematic sectional plain view of the endurance test apparatus. Referring to these figures, the endurance test apparatus 10 is an apparatus for conducting an endurance test on a stent S to be held in a superficial femoral artery and comprises a case 11 in box form, a testing section 12 provided in the case 11, and first and second motors 14 and 15 provided outside the case 11 on the left-hand and right-hand sides as viewed in FIG. 1, as drive means, i.e., drive sources, for enabling the testing section 12 to perform a predetermined operation.

The case 11 has a base 21 as a mounting surface generally in rectangular form as viewed in plain, peripheral wall 22 standing along the peripheral edge of the base 21, and a top wall 23 disposed at the upper end side of the peripheral wall 22 to close from above the space surrounded by the peripheral wall 22.

The testing section 12 has torque transmission means 26 which is joined to a tip end side of a shaft 14A of the first motor 14 positioned on the left-hand side as viewed in FIG. 1, and to which a torque is transmitted from the first motor 14, a drive plate 27 fixed to a tip end of a shaft 15A of the second motor 15 positioned on the right-hand side as viewed in FIG. 1, and first and second lines 28 and 29 (see FIG. 2) joined between the torque transmission means 26 and the drive plate 27.

The torque transmission means 26 has a drive pulley 26A fixed to the tip end side of the shaft 14A to connect to the first line 28 at a lower position as viewed in FIG. 2, a follower pulley 26B rotatably supported at a position above the drive pulley 26A as viewed in FIG. 2 to connect to the second line 29 at a higher position as viewed in FIG. 2, and a belt 26C wrapped around these pulleys 26A and 26B.

The first and second lines 28 and 29 are disposed so as to be bilaterally symmetrical about a horizontal line between their lower and upper positions as viewed in FIG. 2 and are substantially identical in construction to each other. Of the second line 29 at the upper position as viewed in FIG. 2, therefore, the constituent portions identical or similar to those of the first line 28 at the lower position as viewed in FIG. 2 are indicated by the same reference numerals. No description or a simplified description will be made of them.

The first line 28 comprises a simulated blood vessel 31 in tubular form opened at opposite ends in the direction of extension, a first holding member 32 fixed to the drive pulley 26A and holding a left end portion of the simulated blood vessel 31 as viewed in FIG. 1, and a second holding member 33 fixed to the drive plate 27 and holding a right end portion of the simulated blood vessel 31 as viewed in FIG. 1.

The stent S to be evaluated is housed in the simulated blood vessel 31. The simulated blood vessel 31 is formed of an elastic body having elasticity similar to that of a blood vessel in a human body and made of silicone, latex or the like, although the simulated blood vessel 31 is not particularly limited to this. Also, in an initial state before the endurance test in which the first and second motors 14 and 15 are stopped, the simulated blood vessel 31 is supported by the first and second holding members 32 and 33 in a state of being elongated from a natural-length state under the action of a tensile force. An animal blood vessel processed by chemical fixation processing using glutaraldehyde or the like may be used as the simulated blood vessel 31.

Figure 3:
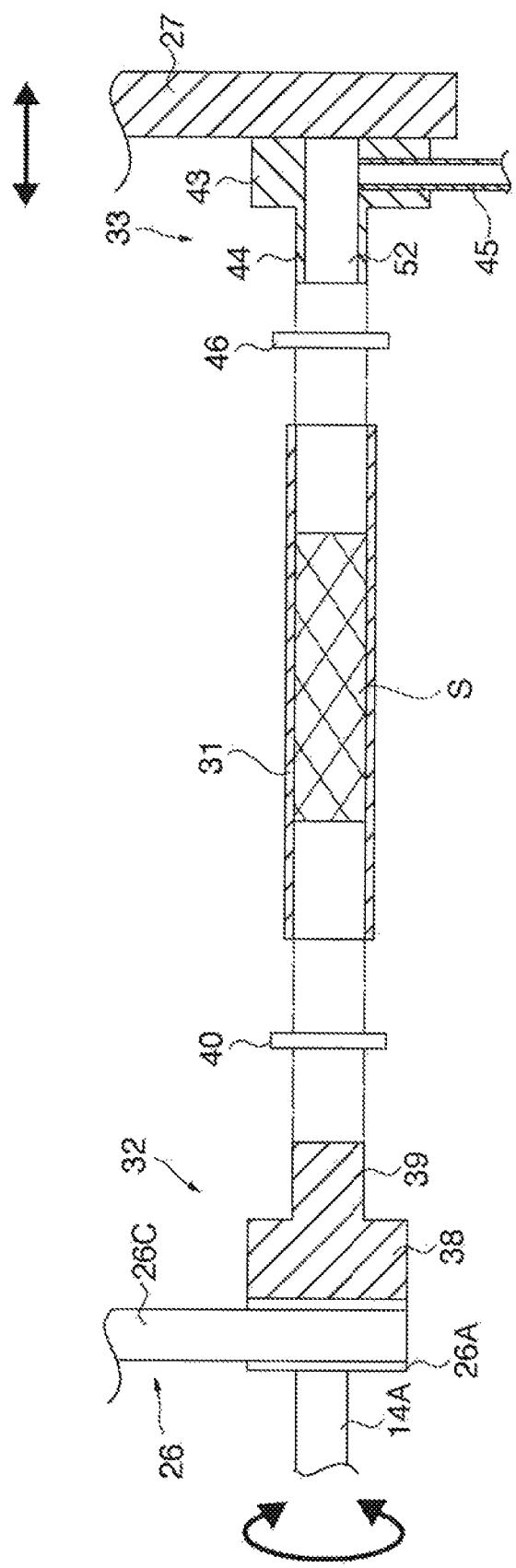
FIG. 3 is an enlarged sectional view of an essential portion taken along line A-A in FIG. 1.

As shown in FIG. 3, the first holding member 32 is formed of a base portion 38 fixed on the drive pulley 26A and a projecting portion 39 joined to a center of the base portion 38 at the right end as viewed in FIG. 3. The outside diameter of the projecting portion 39 is set substantially equal to or slightly larger than the inside diameter of the simulated blood vessel 31. The projecting portion 39 can be fitted in the simulated blood vessel 31 from one end side in the direction of extension of the simulated blood vessel 31 (from the left end as viewed in FIG. 3). In the state where the projecting portion 39 is fitted in the simulated blood vessel 31, a sealing agent such as silicone is interposed between these fitting portions to maintain the elongated state of the simulated blood vessel 31 and to block the inflow of air from the opening portion at the left end as viewed in the figure to the interior. Also, the simulated blood vessel 31 is clamped with a clamp member 40 from the outside of the fitting portions so as not to come off from the first holding member 32.

As shown in FIG. 3, the second holding member 33 is formed of a larger-diameter-side base portion 43 attached to the drive plate 27, a projecting portion 44 joined to a center of the base portion 43 at the left end as viewed in FIG. 3, and an injection passage 45 embedded from the outside of the base portion 43 toward the interior of the base portion 43.

The outside diameter of the projecting portion 44 is set substantially equal to or slightly larger than the inside diameter of the simulated blood vessel 31. The projecting portion 44 can be fitted in the simulated blood vessel 31 from the other end side in the direction of extension of the simulated blood vessel 31 (from the right end as viewed in FIG. 3). In the state where the projecting portion 44 is fitted in the simulated blood vessel 31, a sealing agent such as silicone is interposed between the fitting portions to maintain the elongated state of the simulated blood vessel 31, and the simulated blood vessel 31 is clamped with a clamp member 46, as are those in the case of the above-described fitting between the simulated blood vessel 31 and the first holding member 32. A passage 52 extending along the axial direction of the simulated blood vessel 31 is formed in the base portion 43 and the projecting portion 44. The passage 52 is joined to the injection passage 45. In the state where the simulated blood vessel 31 is mounted on the first and second holding members 32 and 33, therefore, the passage 52 and the injection passage 45 communicate with the internal space of the simulated blood vessel 31. In this state, the opening portion of the simulated blood vessel 31 at the left end as viewed in FIG. 3 are closed with the projecting portion 39.

Through the injection passage 45, a liquid having the same properties as those of blood is injected into the passage 52 by means of a pump, syringe or the like not shown in the figure. In the state where the simulated blood vessel 31 is mounted on the first and second holding members 32 and 33, therefore, the liquid injected from the injection passage 45 into the passage 52 fills the simulated blood vessel 31. In this state, the interior of the simulated blood vessel 31 is in a state of not contacting atmospheric air, thus being simulated in an in-vessel environment in which no air exists.

As the liquid filling the interior of the simulated blood vessel 31, a phosphate buffered saline (PBS), serum of an animal or the like is used, although the liquid filling the interior of the simulated blood vessel 31 is not particularly limited to this. Use of a phosphate buffered saline enables housing of the stent S in the simulated blood vessel 31 in an environment close to the pH environment in a living body as well as prevention of corrosion of the metallic stent S with time. Any other liquid may alternatively be used if there is no problem with the endurance test on the stent S.

As shown in FIG. 2, the above-described second line 29 has the base portion 38 of its first holding member 32 fixed to the follower pulley 26B, and a torque is applied to the base portion 38 by the follower pulley 26B rotating in synchronization with the rotation of the shaft 14A and the drive pulley 26A. In other respects, the construction is the same as that of the first line 28.

In the present embodiment, a servo motor is adopted as the first motor 14, although the first motor 14 is not particularly limited to it. The first motor 14 drives the shaft 14A so that the shaft 14A rotates about its axis, and is controlled so that the rotation of the shaft 14A is repeatedly switched between the normal direction and the reverse direction by predetermined timing. Accordingly, when the shaft 14A rotates, the pulleys 26A and 26B are moved in an interlocked relationship so that each of the first holding members 32 in the first and second lines 28 and 29 connected to the pulleys 26A and 26B is repeatedly rotated in the normal and reverse directions. At this time, the second holding member 33 is not rotated, as described below. Therefore, the first holding member 32 is repeatedly rotated in the normal and reverse directions relative to the second holding member 33, thereby producing torsion deformations in the simulated blood vessel 31.

In the present embodiment, a linear motor such as a voice coil motor is adopted as the second motor 15, although the second motor 15 is not particularly limited to it. The second motor 15 drives the shaft 15A so that the shaft 15A is repeatedly moved in the leftward and rightward directions as viewed in the FIG. 1 by predetermined timing. Accordingly, the second holding member 33 supported on the drive plate 27 connected to the shaft 15A is repeatedly moved in the leftward and rightward directions as viewed in FIG. 1. At this time, the first holding member 32 only rotates and does not move leftward and rightward in synchronization with the second holding member 33, so that the second holding member 33 repeatedly operates by moving closer to and moving away from the first holding member 32 connected through the simulated blood vessel 31 in the leftward and rightward directions as viewed in FIG. 1. Elongating/shortening deformation is thereby also produced in the simulated blood vessel 31.

Thus, the first and second members 32 and 33 constitute supporting means for supporting the simulated blood vessel 31 so that opposite end portions in the direction of extension of the simulated blood vessel 31 act so as to be relatively rotatable and able to move closer to and away from each other.

The flow of the endurance test on the stent S with the above-described endurance test apparatus 10 will next be described.

First, the simulated blood vessel 31 is set in the elongated state by being stretched from the natural-length state. The stent S to be evaluated is inserted into the simulated blood vessel 31 while this elongated state is maintained, and the opposite end portions of the simulated blood vessel 31 in the direction of extension are attached to the first and second holding members 32 and 33 to be set in the state shown in FIG. 1. In this state, the liquid is injected from the injection passage 45 into the passage 52 to fill the interior of the simulated blood vessel 31 with the liquid. When the desired state is attained, injection of the liquid from the injection passage 45 is stopped.

Next, the first motor 14 is driven at a predetermined frequency to repeatedly rotate the first holding member 32 in the normal and reverse directions relative to the second holding member 33, thereby causing the simulated blood vessel 31 connected to the first and second holding members 32 and 33 to repeatedly have torsion deformations in the two directions about its axis.

Simultaneously, the second motor 15 is also driven at a predetermined frequency to cause the second holding member 33 to repeatedly move closer to and away from the first holding member 32 in the leftward and rightward directions as viewed in FIG. 1. When the second holding member 33 moves in the direction of moving closer to the first holding member 32, the straight-line spacing distance between the first and second holding members 32 and 33 decreases, so that the simulated blood vessel 31 deforms elastically in the direction of contraction. Conversely, when the second holding member 33 moves in the direction of moving away from the first holding member 32, the straight-line spacing distance between the first and second holding members 32 and 33 increases, so that the simulated blood vessel 31 deforms elastically in the direction of extension. This sequence of operations is repeatedly performed so that the first and second holding members 32 and 33 repeatedly move closer to and away from each other, thereby repeating the operation to elongate and shorten the simulated blood vessel 31 in the direction of extension. At this time, the outside diameter of the simulated blood vessel 31 itself is increased and reduced by its elasticity.

With this operation to elongate/shorten the simulated blood vessel 31, the volume of the simulated blood vessel 31 varies. With this variation, the liquid pressure therein fluctuates. Thus, the above-described elongating/shortening operation is repeatedly performed to produce a pulsating pressure in the liquid in the simulated blood vessel 31.

The above-described operation is performed for a predetermined time period. Drive of the first and second motors 14 and 15 is thereafter stopped and the stent S is taken out from the interior of the simulated blood vessel 31. The endurance of the stent S is qualitatively evaluated, for example, by observing the damaged state of the surface with a microscope not shown in the figure, measuring a metallic component which has flown out into the solution during use of the stent S with time, and performing qualitative analysis on the elements in the stent S surface.

The inventors of the present invention conducted experiments for verifying the reliability of an endurance test method using the above-described endurance test apparatus 10.

According to clinical data on an examination of the endurance of a certain stent made by holding the stent in the superficial femoral artery of each of a number of patients and by having the patients live in their ordinary ways, breakage of about ¼ of the stents was found after a lapse of one year as a result of the examination. If the stent which was broken in this way breaks in one year from a start of a test made by applying the loads corresponding to the states of use in the patients in the examination of the stents on the endurance test apparatus 10, it can be concluded that the reliability of the endurance test method using the endurance test apparatus 10 is high.

The inventors of the present invention made a study and examination to find that the superficial femoral artery is disposed in a human body with a tensile stress acting therein, and that if a motion such as expansion or flexion of the knee joint occurs in this state, torsion and elongation/shortening act complexly as biomechanical loads on the superficial femoral artery. The inventors therefore made an endurance test on the stent S during a period of time equivalent to a period of about one year in the case of holding the stent S in the superficial femoral artery, by using the above-described endurance test apparatus 10, changing the tensile state of the simulated blood vessel 31 initially set, and causing torsion deformation and elongating/shortening deformation under the load conditions corresponding to the state of use in the above-described patients, as described below.

The test conditions are as described below.

A 72 mm long stent was used as the stent S. As the simulated blood vessel 31 in which the stent S was to be housed, four types of tubes each having an inside diameter of 6 mm and made of silicone were prepared. The simulated blood vessel 31 in which the stent S was housed was fixed through about 10 mm at the opposite ends by the first and second holding members 32 and 33. The effective length of the stent S relating to the deformations of the simulated blood vessel 31 was 72 mm−(10 mm×2)=52 mm.

For the torsion deformation to be given in the simulated blood vessel 31, a condition setting described below was made. First, from the clinical data on humans obtained by the inventors of the present invention, the maximum of the twist angle of the superficial femoral artery (5.3 degrees/cm per 1 cm of the stent S) was adopted. From this, since the effective length of the stent S was 52 mm, drive control of the first motor 14 was performed so that the stent S had twisting deformation at a twist angle of 5.3 degrees×0.52 cm=28 degrees with respect to the entire stent S.

For the elongating/shortening deformation to be given in the simulated blood vessel 31, a condition setting described below was made. An elongation rate (18%) in the subject in which a twist angle of 5.3 degrees was obtained in the clinical data was adopted. From this, stroke control of the second holding member 33, i.e., drive control of the second motor 15, was performed so that the stent S had elongating/shortening deformation of 9.4 mm, which is 18% of the effective length 52 mm of the stent S.

Further, drive of the first and second motors 14 and 15 was controlled so that the number of repeated loading times, i.e., the number of times the operation to twist and elongate/shorten the simulated blood vessel 31 was repeated with the endurance test apparatus 10, was 60 per minute.

The number of days required for testing was set as described below from a statistic indicating that Japanese people's average number of steps per day was 7378 in an examination made by the Ministry of Health, Labour and Welfare. That is, the number of steps per one leg was 7378÷2=3689 and the total number of steps in one year was 3689×365=1346485. That is, the torsion and elongating/shortening loads acting on the superficial femoral artery are applied 1346485 times per one leg in one year. Since the number of repeated loading times in the endurance test apparatus 10 was set to 60 per minute, the necessary number of experiment days was (1346485÷60)÷(60×24)=15.58 and the necessary number of days was set to 16. In other words, the endurance test on the stent S based on the loads for one year acting on the simulated blood vessel 31 by the action of the patient can be performed in 16 days with the present endurance test apparatus 10.

Adjustments or the like including an adjustment of the amount of the liquid with which the interior of the simulated blood vessel 31 was filled were made so that the internal pressure in the simulated blood vessel 31 was equal to an average of 100 mmHg corresponding to the average pulse pressure in the human body.

With respect to each of four types of simulated blood vessels 31 shown below, the endurance test was performed on the stent S under the above-described test conditions. That is, tubes differing in natural length were respectively stretched as the simulated blood vessel 31 to each have a length of 52 mm, and the stent S was inserted in the tube maintained in that state, thus making the test. More specifically, a simulated blood vessel 31 having no tensile force applied thereto and having an elongation rate of 0% with respect to the natural length, a simulated blood vessel 31 having a tensile force applied thereto to set the amount of elongation from the natural length to 16% of the entire length after tensioning and having an elongation rate of 16%, a simulated blood vessel 31 having a tensile force applied thereto to set the amount of elongation to 50% and having an elongation rate of 50% and a simulated blood vessel 31 having a tensile force applied thereto to set the amount of elongation rate to 70% and having an elongation of 70% were prepared. Each simulated blood vessel 31 is repeatedly elongated and shortened between the initial state corresponding to the state after stretching of the simulated blood vessel 31 and the state of being compressed by an amount of 9.4 mm as described above.

The results of the endurance test on the above-described four types of simulated blood vessel 31 are as described below. In the simulated blood vessel 31 having an elongation rate of 0%, none of the breaks appearing in the actual human clinical data was recognized in observation of the surface after the lapse of 16 days from the start of the experiment, but slight damage not appearing in the clinical data was recognized. In the other simulated blood vessels 31, the breaks appearing in the clinical data were recognized within the 16 days from the start of the experiment. More specifically, the break occurred in the simulated blood vessel 31 having an elongation rate of 16% after a lapse of about 2 days from the start of the experiment. The break occurred in the simulated blood vessel 31 having an elongation rate of 50% after a lapse of about 3 days from the start of the experiment. The break occurred in the simulated blood vessel 31 having an elongation rate of 70% after a lapse of about 3 days from the start of the experiment.

According to the above results, breaks of stent S similar to those in the actual clinical data occurred in the simulated blood vessels 31 in which tensile stresses act with respect to the natural length. Also, when the endurance test was conducted on the stents S in a state where a tensile stress acts in the simulated blood vessel 31, the same endurance test results as those in the case of actually holding the stent S in the superficial femoral artery. It was thus verified that the reliability of this endurance test is high.

When the tubes made of silicone were used as described above, the tubes of some of the simulated blood vessels 31 having elongation rates exceeding 70% broke, depending on the material of the simulated blood vessel 31. It was physically impossible to conduct the test on such tubes. On the other hand, in some of the simulated blood vessels 31 having elongation rates not higher than 16%, the length of the vessel becomes shorter than the natural length of the tube in the elongating/shortening process when the above-described elongating/shortening deformation is caused. At this time, a further sag, i.e., a bending deformation in the vertical direction as viewed in FIG. 1, occurs in the simulated blood vessel 31 to produce a load different from those according to the above-described finding about the biochemical loads. Therefore, if the simulated blood vessel 31 is a silicone tube, it is preferable to set the elongation rate to 16% to 70% by considering the fixing margins at the opposite ends. In short, the rate of elongation of the simulated blood vessel 31 set in the endurance test apparatus 10 is not particularly limited, as long as the simulated blood vessel 31 is stretched from the natural length so that any bending deformation cannot occur at the time of elongating/shortening deformation of the simulated blood vessel 31.

Thus, according to the embodiment as described above, the endurance test on the stent S can be conducted in a short time period in a state closer to the case of actually holding the stent S in the superficial femoral artery, and the reliability of the endurance test can be improved.

Since the first and second holding members 32 and 33 are capable of detachably supporting the simulated blood vessel 31, the endurance test on the stent S can be conducted by replacing the simulated blood vessel 31 with any of other simulated blood vessels 31 of various shapes. More specifically, a simulated blood vessel 31 of a different shape or a simulated blood vessel 31 of a different diameter and a different length, such as a simulated blood vessel 31 in straight form generally uniform in inside diameter as a whole or a tapered simulated blood vessel 31 not uniform in inside diameter, can be freely set in the endurance test apparatus 10. There are variations in diameter, length and shape of blood vessels. The stent S endurance test considering such variations among individuals can be easily conducted by interchanging simulated blood vessels 31. While in the present embodiment the behavior of a blood vessel is simulated by considering biomechanical loads in the superficial femoral artery, adaptations to endurance tests on other portions, such as peripheral blood vessels, coronary artery vessels, aorta vessels, carotid artery vessels and AV-shunt vessels, can be easily made by interchanging simulated blood vessels 31 differing in inside diameter for example.

The above-described projecting portions 39 and 44 may be made detachable. In such a case, replacement with selected projecting portions 39 and 44 having outside diameters approximately equal to the inside diameter of the fitted simulated blood vessel 31 is performed. This is more effective in preventing leakage of a liquid from the fitting portions of any simulated blood vessel 31 even in a case where simulated blood vessels 31 of various shapes are used.

The above-described testing section 12 is constituted by the first and second lines 28 and 29. However, the present invention is not limited to this. A line configuration having one line or three or more lines may be adopted. If a configuration of a plurality of lines such as that in the present embodiment is adopted, different types of stents S differing in material and performance can be tested simultaneously with each other and the comparison evaluation of such stent S to be efficiently performed.

The above-described embodiment has been described with reference to the drawings with respect to the structure in which the first holding member 32 is rotated relative to the second holding member 33 and in which the second holding member 33 is moved closer to and away from the first holding member 32. However, the present invention is not limited to this. The first and second holding members 32 and 33 may be made capable of operating in the reversed relationship. In short, any structure may suffice in which the first and second holding members 32 and 33 rotate relative to each other and move closer to and away from each other to simultaneously cause torsion deformation and elongating/shortening deformation in the simulated blood vessel 31.

Further, the above-described endurance test apparatus 10 can be applied to uses other than the above-described performance evaluation of the stent S. For example, an artificial blood vessel inosculated by a doctor or a medical student in anastomosis procedure training may be used as the simulated blood vessel 31 set in the above-described testing section 12. By setting the inosculated portion in the same behaving state as the state after the actual operation, the evaluation with time is enabled.

Also, it is possible to evaluate the endurance of a medical instrument such as the stent S and an inosculated blood vessel by using any other apparatus without using the above-described endurance test apparatus 10. In short, any of various apparatuses and methods can be adopted as long as the same functions as that of the endurance test apparatus 10, i.e., the functions to cause elongating/shortening deformation in the simulated blood vessel 31 given a predetermined tensile force while simultaneously causing torsion deformation in the simulated blood vessel 31, are performed.

The construction of each portion of the apparatus in the present invention is not limited to the illustrated example of the construction. Various changes can be made therein as long as substantially the same functions can be performed.

The invention claimed is:

1. An endurance test apparatus for a medical instrument comprising a simulated blood vessel formed of a predetermined elastic body, supporting means for supporting opposite end portions of the simulated blood vessel in the direction of extension of the simulated blood vessel, the supporting means operating so that the two end portions are relatively rotatable and able to move closer to and away from each other, and drive means for operating the supporting means,
   wherein the simulated blood vessel is supported by the supporting means in a state of being elongated from a natural-length state under the action of a tensile force, and
   wherein the supporting means is driven by the drive means to cause elongating/shortening deformation in the simulated blood vessel in the elongated state while simultaneously causing torsion deformation in the simulated blood vessel.

2. The endurance test apparatus for a medical instrument according to claim 1, wherein the simulated blood vessel is supported by the supporting means in the elongated state disabling generation of bending deformation at the time of the elongating/shortening deformation.

3. An endurance test method for a medical instrument comprising repeatedly performing an operation to cause torsion deformation in a simulated blood vessel formed of a predetermined elastic body and to simultaneously cause elongating/shortening deformation in the simulated blood vessel while a predetermined tensile force is being applied to the simulated blood vessel.

* * * * *

UNITED STATES PATENT AND TRADEMARK OFFICE
CERTIFICATE OF CORRECTION

PATENT NO. : 8,491,308 B2  Page 1 of 1
APPLICATION NO. : 12/676735
DATED : July 23, 2013
INVENTOR(S) : Iwasaki et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 808 days.

Signed and Sealed this
Eighth Day of September, 2015

Michelle K. Lee
*Director of the United States Patent and Trademark Office*